United States Patent [19]

Weinstock et al.

[11] 4,031,125

[45] June 21, 1977

[54] 3-SULFONATE ESTER OF 2,3-DIHYDROXYPROPYLAMINE

[75] Inventors: Leonard M. Weinstock, Belle Mead; Roger J. Tull, Metuchen; Dennis M. Mulvey, Milford, all of N.J.

[73] Assignee: Merck & Co., Inc., Rahway, N.J.

[22] Filed: Oct. 24, 1975

[21] Appl. No.: 625,616

Related U.S. Application Data

[60] Division of Ser. No. 417,301, Nov. 19, 1973, Pat. No. 3,962,338, which is a continuation-in-part of Ser. No. 172,231, Aug. 16, 1971, abandoned, which is a division of Ser. No. 818,474, April 21, 1969, Pat. No. 3,657,237.

[52] U.S. Cl. .......................................... 260/456 A
[51] Int. Cl.² ...................................... C07C 143/68
[58] Field of Search ............................... 260/456 A

[56] References Cited

UNITED STATES PATENTS 2,784,233  3/1957  Kottler et al. ................. 260/584 R

FOREIGN PATENTS OR APPLICATIONS 1,053,193  12/1966  United Kingdom ........... 260/584 R

OTHER PUBLICATIONS

Harris, J. Org. Chem., 28, 745 (1963).

*Primary Examiner*—James O. Thomas, Jr.
*Assistant Examiner*—Nicky Chan
*Attorney, Agent, or Firm*—Daniel T. Szura; J. Jerome Behan

[57] ABSTRACT

Preparation of an optically active alkamine in the sinister configuration, or a derivative of said alkamine, which is reacted with an 3-X-4-chloro(or RO- where R is hydrogen or an alkali metal)-1,2,5-thiadiazole to prepare S-3-X-4-(3-substituted amino-2-hydroxy-propoxy)-1,2,5-thiadiazole beta adrenergic blocking agents. Novel 3-morpholino-4-chloro(or RO-)-1,2,5-thiadiazoles and their preparation also are described.

4 Claims, No Drawings

3-SULFONATE ESTER OF 2,3-DIHYDROXYPROPYLAMINE

This application is a Division of co-pending application Ser. No. 417,301, filed Nov. 19, 1973, now U.S. 3,962,338 which in turn is a Continuation-in-Part of application Ser. No. 172,231, filed Aug. 16, 1971, now abandoned which in turn is a Division of Ser. No. 818,474, filed Apr. 21, 1969, now U.S. Pat. No. 3,657,237.

This invention is concerned with a novel and commercially feasible method for preparing the sinister enantiomer of a 3-amino-1,2-dihydroxypropane, a critical intermediate required in the preparation of the biologically active, S-enantiomer of a 3-X-4-(3-substituted amino-2-hydroxypropoxy)-1,2,5-thiadiazole product substantially devoid of contamination by the rectus enantiomer. Sustantially all of the biological activity of the thiadiazole products resides in the S-enantiomer which was obtained by other workers by the resolution of the racemic product or by the resolution of intermediates employed in their synthesis. These prior methods offer several disadvantages, principally the need to use canogen for the synthesis of the intermediate 3-chloro-4-hydroxy-1,2,5-thiadiazole, an important intermediate, as well as the need to resolve the 3-X-4-(3-substituted amino-2-hydroxypropoxy)-1,2,5-thiadiazole prepared therefrom. It is well known that resolution procedures are uneconomical as they provide low yields of active material because half of the yield of racemic product formed is of no value, and at least some of the desired isomer is not recoverable by feasible large scale procedures.

This invention therefore is concerned principally with the preparation of substantially only the sinister isomer of a 3-amino-1,2-dihydroxypropane utilizing in the synthesis thereof derivatives of optically active carbohydrates which yield the sinister isomer substantially completely free from contamination by the rectus isomer. Optically active starting substances employed in the preparation of this pure sinister isomer are D-glyceraldehyde or isopropylidene-D-glyceraldehyde.

The invention is also concerned with the employment of the pure sinister 3-amino-1,2-dihydroxypropane in the preparation of S-(-)-3-X-4-(3-amino-2-hydroxypropoxy)-1,2,5-thiadiazole free from contamination of its rectus enantiomer thus avoiding all of the difficulties encountered by other workers in the resolution of this end product or the need to resolve racemic compounds at any stage of the synthesis of the biologically active end products, or the need to employ cyanogen in the syntheses of a hydroxy substituted thiadiazole starting material.

The invention also is concerned with a novel method for preparing 3-X-4-chloro-1,2,5-thiadiazole and 3-X-4-hydroxy-1,2,5-thiadiazole, as well as the above novel method for preparing the optically active glycolamines.

According to the principal process of this invention it has been found that S-1,2-dihydroxy-3-amino(or substituted amino)propane can be made in a single step and in quite good yield by the reductive alkylation of the selected amine with D-glyceraldehyde or with isopropylidene-D-glyceraldehyde. The advantage of this process is that when carried out under special conditions only the sinister form of the aminopropanediol is synthesized and it is therefore substantially completely free from contamination by the rectus isomer. This novel process thus provides a maximum yield of this valuable intermediate without the need to resort to resolution and separation procedures which cannot be relied upon to yield pure isomer in maximum yield; at least better than half of the yield always being the unwanted isomer.

The success of the process of this invention was not predictable from the prior art that teaches that glyceraldehyde cyclizes in the presence of base. It was found, however, that reductive alkylation can be effected by hydrogenating a mixture of the selected amine, glyceraldehyde and a hydrogenation catalyst. In order to obtain the aminopropanediol end product in pure sinister configuration it is essential that a solution of the D-glyceraldehyde or isopropylidene-D-glyceraldehyde be added very slowly advantageously dropwise to the mixture of amine, catalyst and solvent during the period of hydrogenation. Addition advantageously is effective over a period of from one to several hours, depending upon the batch size. Hydrogenation advantageously is carried out under a pressure from about 1 to about 10 atmospheres. Any solvent can be employed, suitable ones being tetrahydrofuran, methanol, a mixture of benzene and methanol and the like. Suitable catalysts are platinum, Raney nickel and palladium. While for the present invention one employs an amine of the structure $YNH_2$ and D-glyceraldehyde or isopropylidene-D-glyceraldehyde, it will be appreciated that any amine such as ammonia, a primary or secondary amine, or a nitrogencontaining heterocycle of the structure

can be reductively alkylated with the selected glyceraldehyde by the novel method of this invention.

It is sometimes necessary to use a S-aminopropanediol having an activated hydroxyl group when preparing the S-3-X-4-(3-amino-2-hydroxypropoxy)-1,2,5-thiadiazoles, as will be discussed hereinafter. These S-1,2-dihydroxy-3-amino(or substituted amino)-propanes having an activated hydroxyl group are prepared by reaction with any known and particularly any commercially available sulfonyl halide. The reaction of the S-aminopropanediol with a sulfonyl halide does not change the optical configuration of the product nor does it produce any racemate. As any sulfonyl halide will activate the hydroxyl group and as the sulfonyl moiety is subsequently removed it is not critical that any particular sulfonyl halide be employed to form the sulfonyloxy derivative of the S-1,2-dihydroxy-3-amino(or substituted amino)-propane. For practical purposes, commercially available and inexpensive sulfonyl halides are employed for this purpose and these would fall into the class of alkylsulfonyl halides and benzenesulfonyl halides wherein the benzene moiety can optically be substituted with one or more similar or dissimilar substituents selected from lower alkyl, lower alkoxy, halo, amino and nitro substituents. Among the commercially available sulfonyl halides that can be employed for this purpose there can be mentioned methanesulfonyl chloride, benzenesulfonyl chloride, nitrobenzenesulfonyl chloride, bromobenzenesulfonyl chloride, chlorobenzenesulfonyl chloride, toluenesulfonyl chloride, toluenesulfonyl fluoride, trichlorobenzenesulfonyl chloride, tribromobenzenesulfonyl chloride, fluorobenzenesulfonyl chloride, 4-chloro-2(or 3)- nitrobenzenesulfonyl chloride, hexadecanesulfonyl chloride, 2-mesitylenesulfonyl chloride, methoxybenzenesulfonyl chloride and the like.

A preferred group of aminopropanediols prepared by the above novel procedures are sinister enantiomers of compounds having the structural formula:

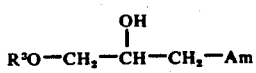

wherein $R^3$ is hydrogen or a sulfonyl group, practically an alkylsulfonyl, benzenesulfonyl or a mono- to tri-substituted benzenesulfonyl wherein the substituents are similar or dissimilar and selected from lower alkyl, lower alkoxy, halo, amino, nitro; and Am is amino, mono- or disubstituted amino, or an N-containing heterocycle of the structure

When designed for use in the synthesis of highly active S-thiadiazole beta-blocking agents, Am is a mono-substituted amino group having the structure —NHY wherein Y is a straight or branched chain lower alkyl (preferably having 1–5 carbon atoms) optionally mono-hydroxy substituted.

The use of these novel S-glycolamines in the syntheses the S-thiadiazole beta-blocking agents is illustrated by the following reaction scheme:

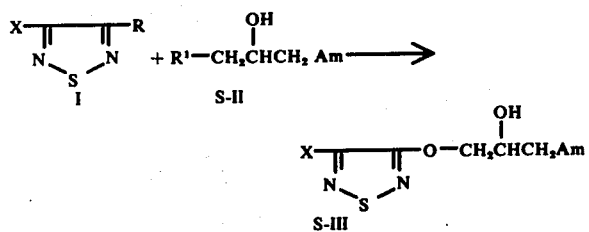

wherein either R or $R^1$ is the reactive hydroxyl group or an alkali metal salt thereof wherein the alkali metal preferably is sodium or potassium the salt form either initially prepared or prepared in situ in the manner hereinafter described. When $R^1$ is HO- or (alkali metal-O-) then R is chloro; when R is OH or a salt thereof, then $R^1$ is the sulfonate derivative of the glycolamine. X in the above structures preferably represents chloro, lower alkyl having 1 to 3 carbon atoms, lower alkoxy having from 1 to 3 carbon atoms, phenyl, benzyl, morpholino, piperidyl, hydroxypiperidyl, and N-lower alkyl-piperazinyl; and Am preferably is -NHY wherein Y is a straight or branched chain lower alkyl having from 1 to 5 carbon atoms which is optionally monohydroxy substituted.

When in the foregoing reaction scheme R in the thiadiazole I is chloro then the

advantageously is selected from S-1-(Y-amino)-2,3-dihydroxypropane, or a salt thereof.

When R in the thiadiazole reactant I is hydroxy, then the hydroxyl group of the

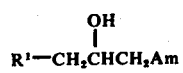

is activated by forming a leaving group, i.e., an easily displaceable group such as a sulfonate of the aforementioned dihydroxypropane.

When R in compound I is chloro and $R^1$ in compound II represents the reactive hydroxyl group, the optically active product, S-III is prepared by the reaction of the thiadiazole I and the S-alkamine, S-II, in the presence of a strong base. Alternately the alkali metal salt of compound II can be preformed. The reaction preferably is carried out at ambient temperature although the reaction mixture either can be heated up to reflux temperature if desired, or cooled to 0° C. A solvent for the reactants is desirable and any conventional solvent can be employed for this purpose; suitable ones being polar aprotic solvents such as simethylformamide (DMF), dimethyl sulfoxide (DMSO), tetrahydrofuran (THF), hexamethylphosphoramide (HMP), lower alkanols and the like. The readily available and relatively inexpensive tert-butanol has been found to be a quite suitable, general purpose solvent for these intermediates. Strong bases that are recommended for use in the reaction are alkali metal alkoxides or alkali metal hydroxides preferably the sodium or potassium alkoxides or hydroxides, or sodium hydride. When product S-III in the form of the free base is obtained as an oil, crystalline material can be prepared by forming the salt by known methods. Suitable salts are those formed with mineral acids or organic acids such as for example the hydrochloride salt, the sulfate salt, the hydrogen maleate salt or other desired mineral or organic acid salt.

When R in compound I represents the reactive hydroxyl group or the alkali metal salt thereof and $R^1$ is a sulfonate group, the reagents are coupled advantageously by combining the reactants in the presence of a solvent and a strong base of the type described above to form the desired product, S-III. Heating the reaction mixture up to the reflux temperature can be employed if desired and any of the usual organic solvents can be used, especially suitable ones being polar aprotic solvents, such as DMF, DMSO, THF, HMP, lower $C_{1-5}$ alkanols and the like.

EXAMPLE I

Step A: Preparation of S(-)-glycolamine

A mixture of tert-butylamine (37.44 g.; 0.513 mole), methanol (150 ml.) and 5% palladium-on-carbon (1.0 g.) is shaken in a hydrogenation bomb under three atmospheres hydrogen pressure. A solution of D-glyceraldehyde (15 g.) in methanol (60 ml.) is added dropwise over a one hour period during hydrogenation. After the addition, the mixture is shaken for an additional 15 hours. The catalyst is removed by filtration and the solvent evaporated in vacuo yielding S(-)-1,2-dihydroxy-3-tert-butylaminopropane [S(-)-glycolamine] in the form of an oil which is crystallized by trituration with ether to give 11.0 g. (45%) yield of product, m.p. 80°–82° C. $[\alpha]_D$-30.1 (1N aqueous HCl).

By replacing the tert-butylamine employed in Step A by an equivalent quantity of isopropylamine, 2,2-dimethylpropylamine, and 1,1-dimethyl-2-hydroxyethylamine and following substantially the same procedure described in Step A, there is obtained, respectively, S-1,2-dihydroxy-3-isopropylaminopropane, S-1,2-dihydroxy-3-(2,2-dimethylpropylamino)propane, and S-1,2-dihydroxy-3-(1,1-dimethyl-2-hydroxyethylamino)-propane.

S(-)-glycolamine also can be prepared by the following method:

PREPARATION OF S(-)-GLYCOLAMINE FROM ISOPROPYLIDENE-D-GLYCERALDEHYDE

Isopropylidene-D-glyceraldehyde (0.276 mole) in 35 ml. of cold tetrahydrofuran is added, with ice bath cooling, over a 1-hour period during hydrogenation to a mixture of tert-butylamine (103 ml.), methanol (103 ml.) and 5% palladium-on-carbon (7.2 g.) in an hydrogenation apparatus under 3 atmospheres hydrogen pressure. The mixture is hydrogenated at ambient temperature until the absorption of hydrogen ceases. The catalyst then is removed by filtration and washed with methanol (52 ml.) and the combined filtrates treated with 6N hydrochloric acid (350 ml.) with cooling. The mixture then is distilled until a vapor temperature of 98° ± 1° C is reached and then refluxed one hour. The solution then is cooled to 0° C. and treated with sodium hydroxide pellets (140 g.) keeping the temperature under 35° C. Thereafter the mixture is treated with water (140 ml.) and extracted with four 175 ml. portions of methylene chloride. The combined extracts are dried over magnesium sulfate and evaporated to a thick crystalline slurry which is flushed twice with ether (50 ml.) and filtered at 0°-5° C. After drying at 35° C. in vacuo there is obtained 28.5 g. (70%) of S(-)-glycolamine.

Step B: Preparation of 3-morpholino-4-chloro-1,2,5-thiadiazole 3,4-Dichloro-1,2,5-thiadiazole (100.0 g.; 0.645 mole) is added dropwise over a 30-minute period at 105°-110° C. to morpholine (224 ml.; 2.58 mole). After the addition, the mixture is stirred 2 hours at 105°-110° C., then cooled to 15° C. and quenched with water (250 ml.). This mixture then is made acidic with concentrated hydrochloric acid (250 ml.) whereupon an insoluble oil soon crystallizes to a heavy solid mass. After crystallization is complete the solid is filtered and washed with water and then dried at 35° C. in vacuo yielding 125.5 g. (95%) of 3-morpholino-4-chloro-1,2,5-thiadiazole, m.p. 43°-45° C.

Step C: Preparation of S(-)-3-morpholino-4-(3-tert-butylamino-2-hydroxypropoxy)-1,2,5-thiadiazole and its hydrogen maleate salt A mixture of 3-morpholino-4-chloro-1,2,5-thiadiazole (20.57 g.) and S(-)-glycolamine (14.72 g.) in anhydrous tert-butanol (50 ml.) is heated to reflux under a nitrogen atmosphere. A solution of potassium tert-butoxide in tertbutanol (100 ml. of 1M solution or equivalent) is added in 10 ml. portions and the mixture refluxed 10 minutes between additions. After the last addition the mixture is refluxed an additional 10 minutes, then cooled to 60° C., and treated with 6N hydrochloric acid (50 ml.) in a thin stream while maintaining good cooling. An additional 50 ml. of water is added and the tert-butanol is evaporated in vacuo leaving an oil-water residue. This residue is extracted with one 50 ml. portion and one 20 ml. portion of methylene chloride and the combined organic layers are backwashed with two 50 ml. portions of 4N hydrochloric acid. The combined acid layers are made alkaline with excess potassium carbonate (approximately 80 g.) and extracted with two 50 ml. portions of ether. The combined ether layers are washed with two 20 ml. portions of water, dried over magnesium sulfate and evaporated in vacuo to give 13.7 g. of S(-)-3-morpholino-4-(3-tert-butylamino-2-hydroxypropoxy)-1,2,5-thiadiazole in the form of an oil.

This oil is dissolved in 50 ml. of tetrahydrofuran, treated with charcoal (1.5 g.), filtered, and the cake washed with 20 ml. of tetrahydrofuran. To this solution is added maleic acid [5.0 g.; 1 mole equivalent per mole of S(-)-3-morpholino-4-(3-tert-butylamino-2-hydroxypropoxy)-1,2,5-thiadiazole] dissolved in tetrahydrofuran (25 ml.). The mixture then is seeded and aged 1 hour at 25° C. The crystallized hydrogen maleate salt is separated by filtration, washed with tetrahydrofuran and dried at 50° C. in vacuo to give 7.3 g. of S(-)-3-morpholino-4-(3-tert-butylamino-2-hydroxypropoxy)-1,2,5-thiadiazole hydrogen maleate, m.p. 195°-198° C. (sample inserted at 190° C. and heated at rate of 3°/min.). $[\alpha]_{405} -12°$ [C = 4, 1N HCl], equivalent weight 429-431 (titrated with base), calculated 432.

By employing quantities of the following reaction pairs
1. 3-morpholino-4-chloro-1,2,5-thiadiazole and S-1,2-dihydroxy-3-isopropylaminopropane,
2. 3-(4-methylpiperazinyl)-4-chloro-1,2,5-thiadiazole and S(-)-glycolamine,
3. 3-piperidyl-4-chloro-1,2,5-thiadiazole and S-1,2-dihydroxy-3-isopropylaminopropane,
4. 3-piperidyl-4-chloro-1,2,5-thiadiazole and Sc-)-glycolamine, and
5. 3-(4-hydroxypiperidyl)-4-chloro-1,2,5-thiadiazole and S(-)-glycolamine equivalent to the quantity used in Step C and following substantially the same procedure described in Step C, there is obtained, respectively,
1. S-3-morpholino-4-(3-isopropylamino-2-hydroxypropoxy)-1,2,5-thiadiazole and its hydrogen maleate salt,
2. S-3-(4-methylpiperazinyl)-4-(3-tert-butylamino-2-hydroxypropoxy)-1,2,5-thiadiazole and its hydrogen maleate salt,
3. S-3-piperidyl-4-(3-isopropylamino-2-hydroxypropoxy)-1,2,5-thiadiazole and its hydrogen maleate salt,
4. S-3-piperidyl-4-(3-tert-butylamino-2-hydroxypropoxy)-1,2,5-thiadiazole and its hydrogen maleate salt, and
5. S-3-(4-hydroxypiperidyl)-4-(3-tert-butylamino-2-hydroxypropoxy)-1,2,5-thiadiazole and its hydrogen maleate salt.

EXAMPLE 2

Step A: Preparation of S(-)-glycolamine-1-toluenesulfonate

A solution of S(-)-glycolamine (4.0 g.), prepared as described in Example 1, Step A, and pyridine hydrochloride (3.14 g.) in pyridine (8 ml.) is treated with p-toluenesulfonyl chloride (5.31 g.). The mixture is stirred for one-half hour at 25°-30° C. and then poured into 50 ml. of cold water. The solution is treated with potassium carbonate (1.92 g.) and the pyridine evaporated in vacuo at a temperature between 55°-60° C. The aqueous residue is treated with potassium carbonate (4.5 g.) and the mixture extracted with methylene chloride (50 ml.). Evaporation of the dried extract provides 6.2 g. (75% yield) of S(-)glycolamine-1-toluenesulfonate [S(-)-1-toluenesulfonyloxy-2-hydroxy-3-tert-butylaminopropane], m. p. 91°–93° C.

By replacing the S(-)-glycolamine and the p-toluenesulfonyl chloride by equivalent quantities of the following reaction pairs:

1. S-1,2-dihydroxy-3-isopropylaminopropane and benzenesulfonyl chloride,
2. S-1,2-dihydroxy-3-(2,2-dimethylpropylamino)propane and methylsulfonyl chloride and/or other lower alkylsulfonyl chloride,
3. S-1,2-dihydroxy-3-(1,1-dimethyl-2-hydroxyethylamino)propane and p-chlorophenylsulfonyl chloride, there is obtained respectively, 1. S-1-benzenesulfonyloxy-2-hydroxy-3-isopropylaminopropane,
2. S-1-methylsulfonyloxy-2-hydroxy-3-(2,2-dimethylpropylamino)propane or other lower alkylsulfonyloxy derivative, and
3. S-1-(p-chlorophenylsulfonyloxy)-2-hydroxy-3-(1,1-dimethyl-2-hydroxyethylamino)propane.

Any other sulfonyl halide, particularly (through not necessarily) any of the commerically available sulfonyl halides identified hereinabove can be employed with equal success if substituted in the process of this example for reaction with any desired S-1,2-dihydroxy-3-amino(or substituted amino)propane to provide the sulfonyloxy derivatives thereof which upon reaction with the appropriate 1,2,5-thiadiazole according to Step C of this example gives product S-III.

Step B: Preparation of
3-morpholino-4-hydroxy-1,2,5-thiadiazole

3-Morpholino-4-chloro-1,2,5-thiadiazole (125.5 g.) prepared as described in Example 1, Step B, is added to 2.5N sodium hydroxide (1 liter) in dimethyl sulfoxide (100 ml.). The mixture is refluxed with stirring for about 3 hours and the solution then is cooled to 15° C. and made acidic with concentrated hydrochloric acid (250 ml.). The precipitated material is removed by filtration at 15° C. and slurried well with water. The solid material then is dried to constant weight thus providing 108.7 g. of 3-morpholino-4-hydroxy-1,2,5-thiadiazole, m.p. 198°–200° C. (dec.).

Step C: Preparation of
S(-)-3-morpholino-4-(3-tert-butylamino-2-hydroxypropoxy)-1,2,5-thiadiazole S(-)-glycolamine-1-toluenesulfonate (3.45 g.; 11.45 mole) is added to 0.805N methanolic sodium methoxide (15 ml.) at 0° C. The mixture is stirred for 15 minutes at 0.5° C., treated with 3-morpholino-4-hydroxy-1,2,5-thiadiazole (4.29 g.) and then refluxed for 16 hours. The solvent is evaporated in vacuo and the residue treated with excess potassium carbonate. The insoluble oil is extracted with ether, the ether extracts dried and evaporated to provide S(-)-3-morpholino-4-(3-tert-butylamino-2-hydroxypropoxy)-1,2,5-thiadiazole in 35% yield.

By replacing the S(-)-glycolamine-1-toluenesulfonate and the 3-morpholino-4-hydroxy-1,2,5-thiadiazole employed in Step C by equivalent quantities of the following reaction pairs:

1. S(-)-glycolamine-1-toluenesulfonate and 3-chloro-4-hydroxy-1,2,5-thiadiazole or its alkali metal salt,
2. S-1-benzenesulfonyloxy-2-hydroxy-3-isopropylaminopropane and 3-chloro-4-hydroxy-1,2,5-thiadiazole or its alkali metal salt,
3. S-1-benzenesulfonyloxy-2-hydroxy-3-isopropylaminopropane and 3-ethyl-4-hydroxy-1,2,5-thiadiazole or its alkali metal salt,
4. S(-)-glycolamine-1-toluenesulfonate and 3-ethyl-4-hydroxy-1,2,5-thiadiazole or its alkali metal salt,
5. S-1-(p-chlorophenylsulfonyloxy)-2-hydroxy-3-(1,1-dimethyl-2-hydroxyethylamino)propane and 3-ethyl-4-hydroxy-1,2,5-thiadiazole or its alkali metal salt,
6. S-1-benzenesulfonyloxy-2-hydroxy-3-isopropylaminopropane and 3-ethoxy-4-hydroxy-1,2,5-thiadiazole or its alkali metal salt,
7. S(-)-glycolamine-1-toluenesulfonate and 3-ethoxy-4-hydroxy-1,2,5-thiadiazole or its alkali metal salt,
8. S-1-methylsulfonyloxy-2-hydroxy-3-(2,2-dimethylpropylamino)propane or other lower alkylsulfonyloxy derivative and 3-ethoxy-4-hydroxy-1,2,5-thiadiazole or its alkali metal salt,
9. S-1-benzenesulfonyloxy-2-hydroxy-3-isopropylaminopropane and 3-phenyl-4-hydroxy-1,2,5-thiadiazole or its alkali metal salt,
10. S(-)-glycolamine-1-toluenesulfonate and 3-phenyl-4-hydroxy-1,2,5-thiadiazole or its alkali metal salt,
11. S(-)-glycolamine-1-toluenesulfonate and 3-benzyl-4-hydroxy-1,2,5-thiadiazole or its alkali metal salt, and following substantially the same procedure described in Step C, there is obtained, respectively, 1. S-3-chloro-4-(3-tert-butylamino-2-hydroxypropoxy)-1,2,5-thiadiazole,
2. S-3-chloro-4-(3-isopropylamino-2-hydroxypropoxy)-1,2,5-thiadiazole,
3. S-3-ethyl-4-(3-isopropylamino-2-hydroxypropoxy)-1,2,5-thiadiazole,
4. S-3-ethyl-4-(3-tert-butylamino-2-hydroxypropoxy)-1,2,5-thiadiazole,
5. S-3-ethyl-4-[3-(1,1-dimethyl-2-hydroxyethylamino)-2-hydroxypropoxy]-1,2,5-thiadiazole,
6. S-3-ethoxy-4-(3-isopropylamino-2-hydroxypropoxy)-1,2,5-thiadiazole,
7. S-3-ethoxy-4-(3-tert-butylamino-2-hydroxypropoxy)-1,2,5-thiadiazole,
8. S-3-ethoxy-4-[3-(2,2-dimethylpropylamino)-2-hydroxypropoxy]-1,2,5-thiadiazole,
9. S-3-phenyl-4-(3-isopropylamino-2-hydroxypropoxy)-1,2,5-thiadiazole,
10. S-3-phenyl-4-(3-tert-butylamino-2-hydroxypropoxy)-1,2,5-thiadiazole,
11. S-3-benzyl-4-(3-tert-butylamino-2-hydroxypropoxy)-1,2,5-thiadiazole.

The S-3-X-4-[3-(Y-amino)-2-hydroxypropoxy]-1,2,5-thiadiazole compounds prepared from the novel S-glycolamines of this invention by the process described above as well as their salts have been found to exhibit β-adrenergic blocking properties and are thus useful in the management of angina pectoris. Because of this property the optically active products are useful for the control of tachycardia that may be drug induced (as by isoproterenol) or brought about by physiological conditions.

The optically active products particularly in the form of their salts can be prepared in pharmaceutical formulations suitable for oral or parenteral administration and also can be combined with other active ingredients for simultaneous administration. No special problems are involved in preparing suitable formulations of the optically active compounds or salts thereof and methods generally employed for this purpose, which are known to those skilled in this art, are entirely suitable. Dosage units of from about 2 mgs. to about 10 mgs. can be provided for the symptomatic adjustment of dosage of the optically active substances by the physician depending upon the age and condition of the patient.

What is claimed is:

1. An optically active glycolamine in the sinister configuration substantially completely free from the rectus isomer having the structure

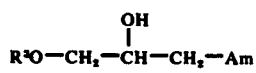

wherein $R^3$ is lower alkylsulfonyl, benzenesulfonyl or mono- to tri-substituted benzenesulfonyl wherein the substituents are similar or dissimilar and are lower alkyl, lower alkoxy, halo, amino or nitro; Am is the amino group or monoloweralkyl-substituted amino.

2. An optically active glycolamine in the sinister configuration substantially completely free from the rectus isomer having the structure

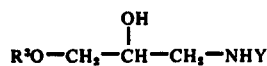

wherein $R^3$ is lower alkylsulfonyl, benzenesulfonyl or mono- to tri-substituted benzenesulfonyl wherein the substituents are similar or dissimilar and are lower alkyl, lower alkoxy, halo, amino or nitro; and Y is a straight or branched chain lower alkyl.

3.

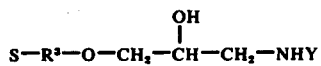

substantially completely free from contamination with its rectus isomer wherein $R_3^3$ is lower alkylsulfonyl, benzenesulfonyl or mono- to tri-substituted benzenesulfonyl wherein the substituents are similar or dissimilar and are lower alkyl, lower alkoxy, halo, amino or nitro; and Y is branched chain lower alkyl.

4. S(-)-1-toluenesulfonyloxy-2-hydroxy-3-tert-butylaminopropane substantially completely free from contamination with its rectus isomer.

* * * * *